(12) United States Patent
Makuuchi et al.

(10) Patent No.: US 7,990,529 B2
(45) Date of Patent: Aug. 2, 2011

(54) DETECTION CIRCUIT AND FOREIGN MATTER INSPECTION APPARATUS FOR SEMICONDUCTOR WAFER

(75) Inventors: Masami Makuuchi, Yokohama (JP); Ritsuro Orihashi, Tokyo (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 196 days.

(21) Appl. No.: 12/266,663

(22) Filed: Nov. 7, 2008

(65) Prior Publication Data

US 2009/0122305 A1 May 14, 2009

(30) Foreign Application Priority Data

Nov. 9, 2007 (JP) ................................ 2007-292106

(51) Int. Cl.
*G01N 21/00* (2006.01)

(52) U.S. Cl. .................................................. 356/237.1

(58) Field of Classification Search ..... 356/237.1–237.5
See application file for complete search history.

(56) References Cited

U.S. PATENT DOCUMENTS

| | | | | |
|---|---|---|---|---|
| 3,907,440 A | * | 9/1975 | Eichenberger et al. ....... 356/429 |
| 5,313,169 A | * | 5/1994 | Fouche et al. ................. 329/302 |
| 6,191,849 B1 | * | 2/2001 | Maeshima et al. .......... 356/237.1 |
| 6,509,966 B2 | * | 1/2003 | Ishiguro ..................... 356/237.2 |
| 7,602,482 B2 | * | 10/2009 | Matsui ........................ 356/237.3 |
| 2004/0124832 A1 | * | 7/2004 | Makuuchi et al. ............. 324/212 |

FOREIGN PATENT DOCUMENTS

JP 08-145899 6/1996

* cited by examiner

*Primary Examiner* — Michael P Stafira
*Assistant Examiner* — Isiaka O Akanbi
(74) *Attorney, Agent, or Firm* — Antonelli, Terry, Stout & Kraus, LLP.

(57) ABSTRACT

In a foreign matter inspection apparatus for a semiconductor wafer, a PMT which detects reflection light, an amplifier which amplifies a signal detected by the PMT and in which response characteristics of amplification are controlled by a control signal, an A/D converter which converts the signal amplified by the amplifier into a predetermined code and outputs the code, a control circuit which generates a control signal based on information of the semiconductor wafer having a correlation with the reflection light, and a data processing circuit which detects a foreign matter on the semiconductor wafer based on the code output from the A/D converter are provided.

6 Claims, 6 Drawing Sheets

DETECTION CIRCUIT AND FOREIGN MATTER INSPECTION APPARATUS FOR SEMICONDUCTOR WAFER

CROSS-REFERENCE TO RELATED APPLICATION

The present application claims priority from Japanese Patent Application No. JP 2007-292106 filed on Nov. 9, 2007, the content of which is hereby incorporated by reference into this application.

TECHNICAL FIELD OF THE INVENTION

The present invention relates to a foreign matter inspection apparatus for a semiconductor wafer, which performs foreign matter inspection by means of a response signal from an object to be inspected such as a semiconductor wafer, and more particularly to a signal detection technique in a detection circuit thereof.

BACKGROUND OF THE INVENTION

Figure 5:
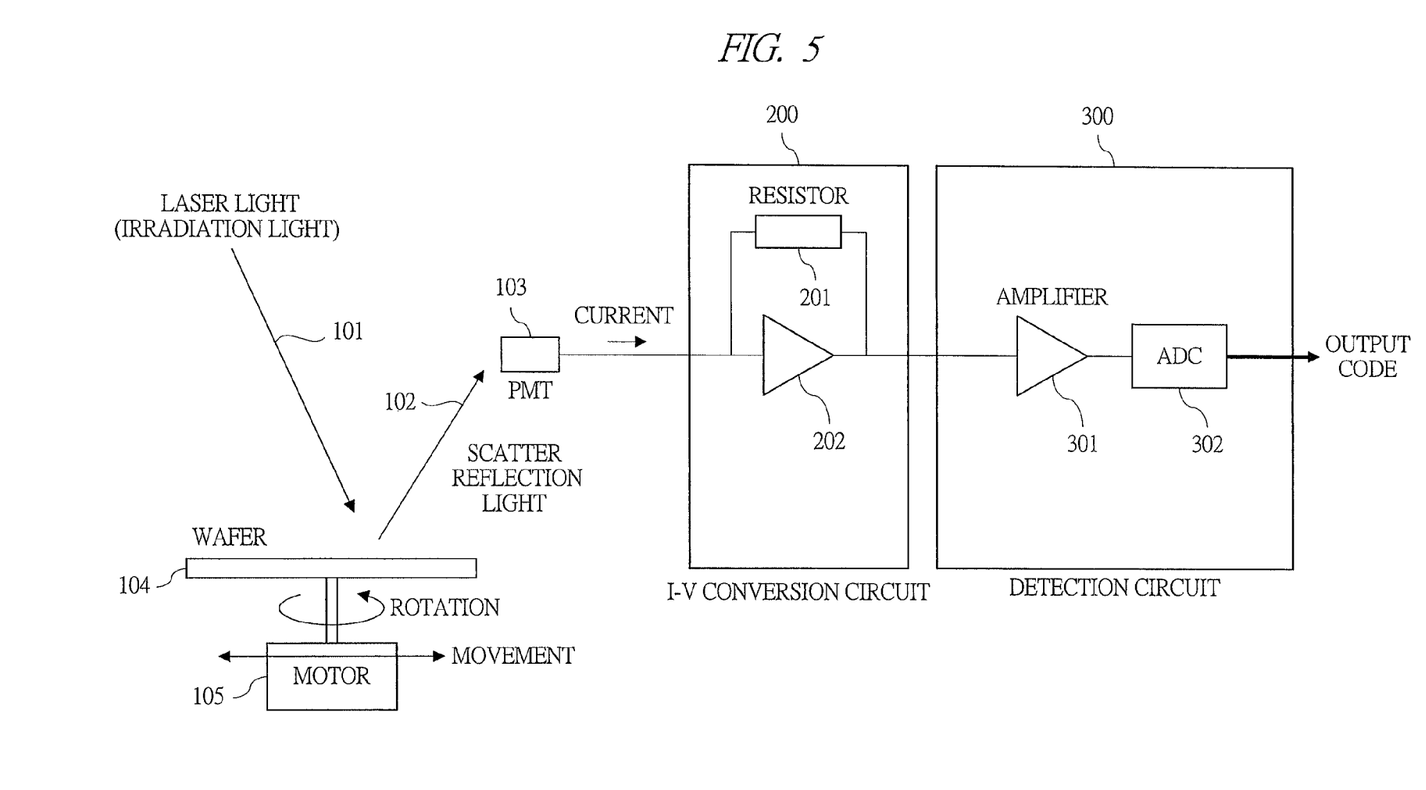
FIG. 5 is a diagram schematically showing a detection circuit of a foreign matter inspection apparatus for a semiconductor wafer according to the conventional technology.

A detection circuit of a conventional foreign matter inspection apparatus for a semiconductor wafer examined by the inventors of the present invention as a premise of the present invention will be schematically described with reference to FIG. 5. FIG. 5 is a diagram schematically showing the detection circuit of the conventional foreign matter inspection apparatus for a semiconductor wafer.

More specifically, in the conventional foreign matter inspection apparatus for a semiconductor wafer, laser light 101 is irradiated as irradiation light onto a rotating semiconductor wafer 101, scatter reflection light 102 from a foreign matter or the like present on the semiconductor wafer 104 is detected by a photo multiplier tube (PMT) 103.

The PMT 103 multiplies the incident light by the photo multiplier effect and outputs a current in accordance with the incident light intensity, and it outputs the foreign matter detection signal current based on the scatter reflection light 102 from a foreign matter or the like.

In a detection unit including an I-V conversion circuit 200 and a detection circuit 300, the I-V conversion circuit 200 including a resistor 201 and an operational amplifier 202 performs the conversion to a detection voltage signal based on the foreign matter detection signal current.

Further, in the detection circuit 300, the detection voltage signal is amplified by an amplifier 301 and the voltage is converted into a digital value by use of an A/D converter 302. Thereafter, the digital value is output to a data processing circuit (not shown) as an output code to determine the foreign matter or the like.

It is generally said that the intensity of the scatter reflection light from the foreign matter with a minute diameter is proportional to the sixth power of the diameter of the foreign matter. Therefore, when the foreign matter is to be detected by the light irradiation and the scatter reflection light thereof, the detection signal becomes minute as the size of the foreign matter on the semiconductor wafer to be inspected becomes smaller, and the wide dynamic range is required in accordance with the amplitude range of the detection signal in the detection circuit 300 to detect the detection signal.

Further, when the rotation speed of the semiconductor wafer is increased in order to shorten the inspection time of the semiconductor wafer, the scanning speed on the surface of the semiconductor wafer is also increased, the change ratio of the detection signal per unit time is increased, and the speeding-up is also required in the detection unit.

Incidentally, since the basic trade-off relation exists between the speed and the dynamic range in the A/D converter 302 in general, the dynamic range of the A/D converter 302 is reduced and the minimum resolution is increased as the speed is increased.

Accordingly, as the conventional technology, Japanese Patent Application Laid-Open Publication No. 8-145899 (Patent Document 1) proposes the method in which a plurality of amplifiers that amplify the detection current at different amplification factors are disposed in parallel, and the dynamic range is expanded by the output of the appropriate range of the plurality of amplifier outputs.

SUMMARY OF THE INVENTION

According to the technology of the patent document 1, by disposing the A/D converter for each of the ranges managed by the plurality of amplifiers, even in the state where the dynamic range of each A/D converter is restricted due to the speeding-up, the expansion of the dynamic range can be achieved as the whole detection unit.

Figure 6:
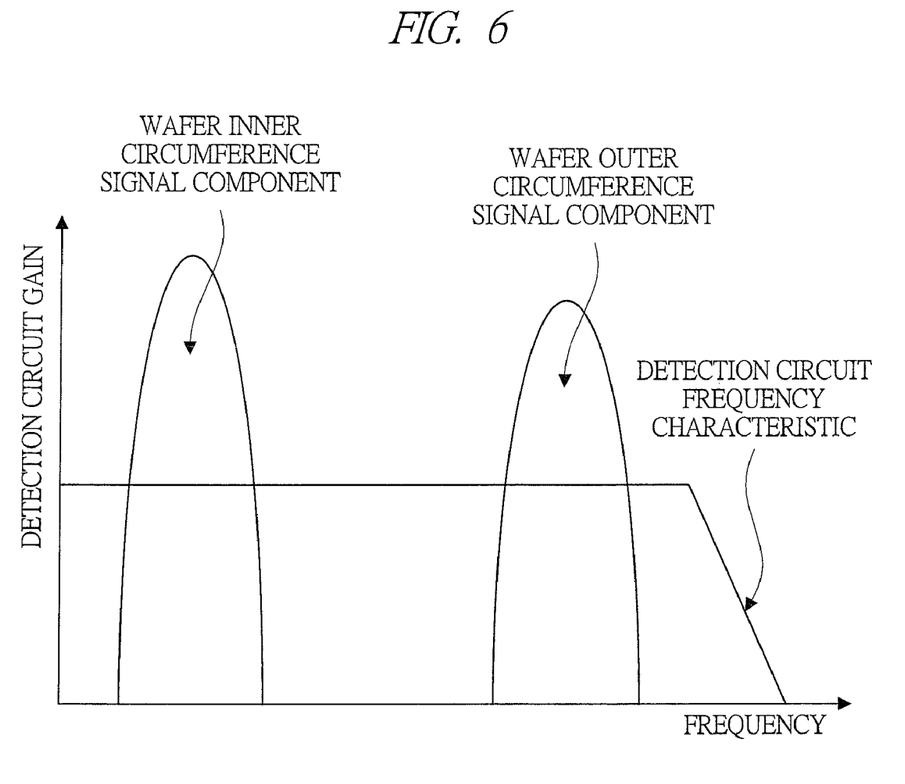
FIG. 6 is an explanatory diagram for describing the frequency characteristics of the detection circuit of the foreign matter inspection apparatus for a semiconductor wafer according to the conventional technology.

However, with regard to the minute foreign matter, a noise is superposed on the detection signal, and thus the improvement in the signal detection accuracy cannot be achieved even when the amplification factor of the detection circuit is increased. In particular, the signal frequency component of the foreign matter detection signal from the semiconductor wafer that is rotating at a constant rotation speed is changed in accordance with the radius position of the foreign matter as shown in FIG. 6. Therefore, when the detection characteristics are set so that the outer circumference signal from the semiconductor wafer having the high-frequency signal component can be detected, in the detection of the inner circumference signal from the semiconductor wafer in which the signal components are concentrated at the lower frequency, the frequency band of the detection circuit becomes an unnecessarily wide band. As a result, the contained noise cannot be restrained and the detection accuracy is deteriorated.

The present invention has been made in consideration of the above-mentioned problems, and an object of the present invention is to provide a detection circuit capable of detecting signals with high accuracy by performing variable control of the detection circuit characteristics in accordance with the conditions of the detection signal, and a foreign matter inspection apparatus for a semiconductor wafer using the detection circuit.

The novel characteristics of the present invention will be apparent from the description of this specification and the accompanying drawings.

The typical ones of the inventions disclosed in this application will be briefly described as follows.

That is, the present invention is typically a foreign matter inspection apparatus for a semiconductor wafer that comprises: an amplifier which amplifies a signal detected by a reflection light detector and in which response characteristics of amplification are controlled by a control signal; an A/D converter which converts the signal amplified by the amplifier into a predetermined code and outputs the code; and a control circuit which generates the control signal based on information of the semiconductor wafer having a correlation with the reflection light.

These and other objects, features and advantages of the invention will be apparent from the following more particular description of preferred embodiments of the invention, as illustrated in the accompanying drawings.

DESCRIPTIONS OF THE PREFERRED EMBODIMENTS

Hereinafter, embodiments of the present invention will be described in detail with reference to the accompanying drawings. Note that components having the same function are denoted by the same reference numbers throughout the drawings for describing the embodiments, and the repetitive description thereof will be omitted.

First Embodiment

Figure 1:
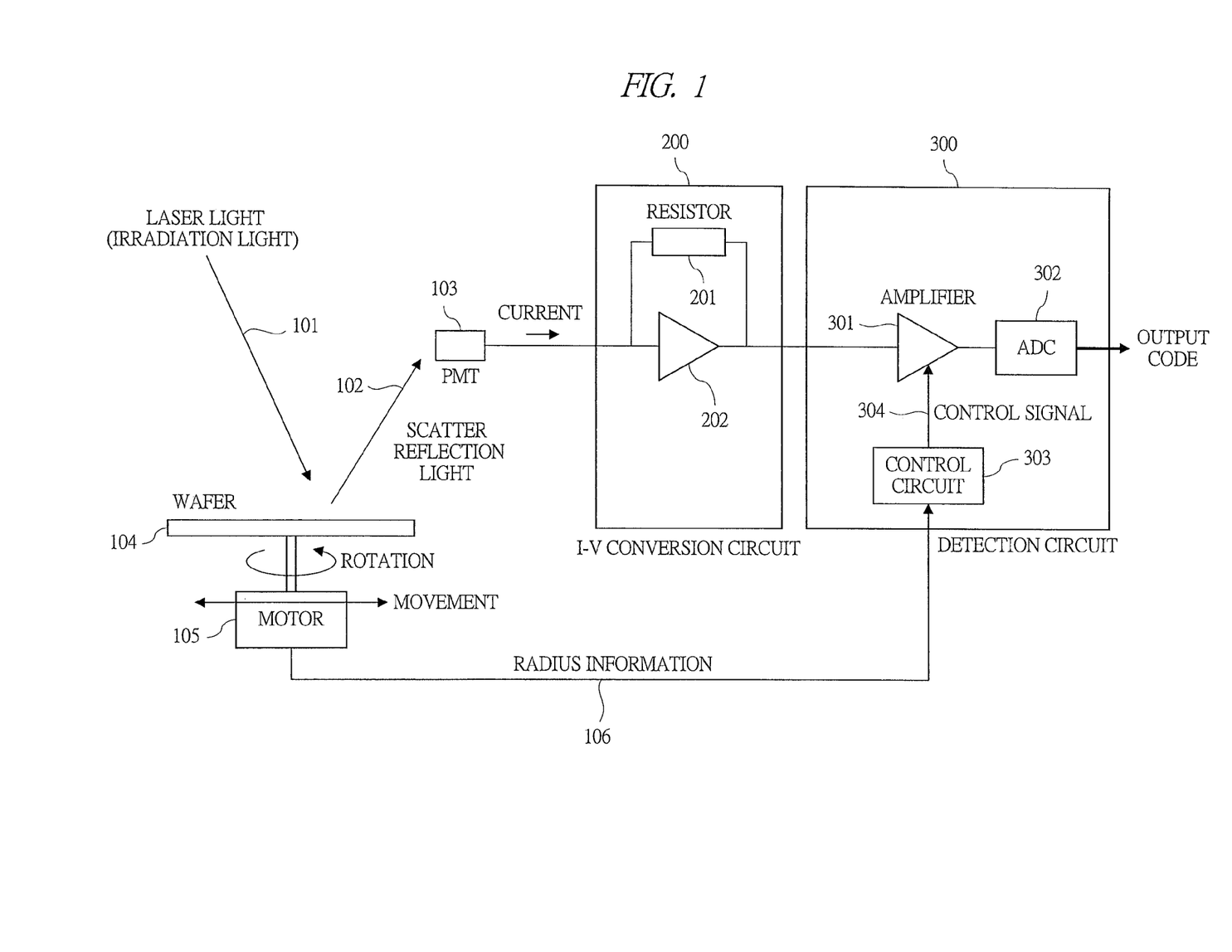
FIG. 1 is a configuration diagram showing the configuration of a foreign matter inspection apparatus for a semiconductor wafer according to the first embodiment of the present invention.

The configuration of the foreign matter inspection apparatus for a semiconductor wafer according to the first embodiment of the present invention will be described with reference to FIG. 1. FIG. 1 is a configuration diagram showing the configuration of the foreign matter inspection apparatus for a semiconductor wafer according to the first embodiment of the present invention.

In FIG. 1, the foreign matter inspection apparatus for a semiconductor wafer comprises: a motor 105 which rotates a semiconductor wafer 104, which is an object to be inspected, held by a wafer holding mechanism (not shown); a movement mechanism (not shown) which controls the movement of the motor 105 and outputs radius information 106 (information having a correlation with the response signal from the object to be inspected) of the semiconductor wafer 104 to be inspected based on the amount of movement; laser light 101 to be irradiated onto the semiconductor wafer 101; photo multiplier tube (PMT) which is a reflection light detector that detects scatter reflection light 102 generated by irradiating the laser light 101 onto the semiconductor wafer 104 when a foreign matter or the like (not shown) is present on the semiconductor wafer 104 and outputs current in accordance with the intensity of the scatter reflection light 102; an I-V conversion circuit 200 which includes a resistor 201 and an operational amplifier 202 and converts the signal current output from the photo multiplier tube (PMT) 103 into voltage to output the same; a detection circuit 300 that amplifies the voltage output from the I-V conversion circuit 200 by an amplifier 301 and converts the amplified voltage to a predetermined code by an A/D converter 302 to output the same; and a data processing circuit (not shown) that inputs the output code from the detection circuit 300 and determines the foreign matter or the like.

Further, the detection circuit 300 includes a control circuit 303 that outputs a control signal 304 for controlling the response characteristics of the amplifier 301 based on the radius information 106.

Figure 2:
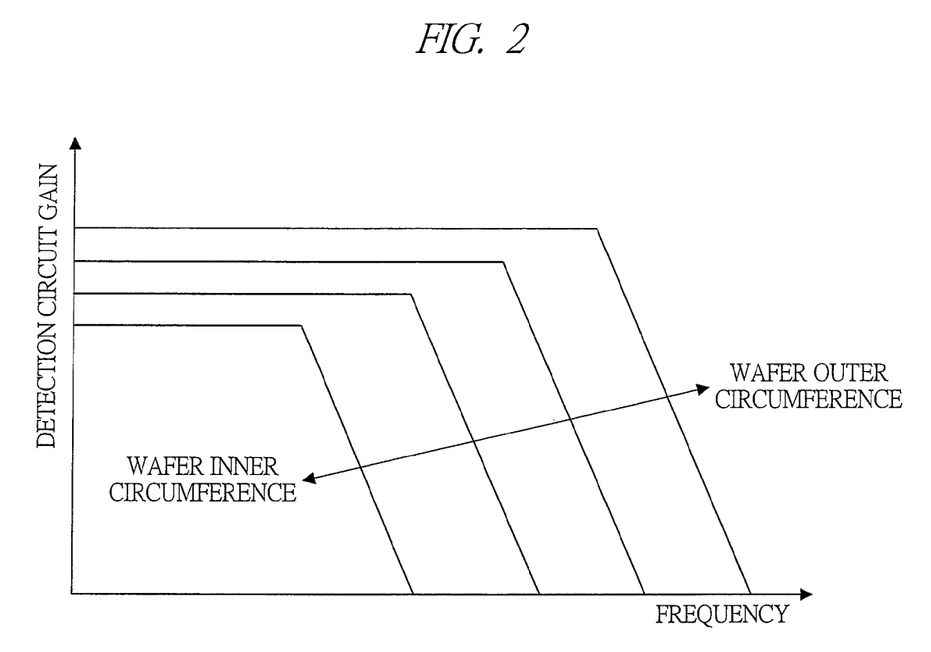
FIG. 2 is a diagram showing frequency characteristics in a detection circuit of the foreign matter inspection apparatus for a semiconductor wafer according to the first embodiment of the present invention.

Next, the operation of the foreign matter inspection apparatus for a semiconductor wafer according to the first embodiment of the present invention will be described with reference to FIGS. 1, 2 and 6. FIG. 2 is a diagram showing the frequency characteristics of the detection circuit in the foreign matter inspection apparatus for a semiconductor wafer according to the first embodiment of the present invention.

First, in the foreign matter inspection apparatus, the laser light 101 is irradiated onto the semiconductor wafer 104, the semiconductor wafer 104 is rotated, and the motor 105 is moved so as to change the radius position of the semiconductor wafer 104. By this means, the track of the laser light 101 irradiated onto the surface of the semiconductor wafer 104 forms a spiral shape, and thus the full-surface inspection of the semiconductor wafer 104 is performed.

When the radius position of the semiconductor wafer 104 is changed while keeping the rotation speed of the semiconductor wafer 104 constant, the linear velocity at the irradiation point of the laser light 101 in the outer circumference of the semiconductor wafer 104 is high, and the frequency components of the scatter reflection light 102 from the foreign matter on the wafer surface are concentrated on the high-frequency range as shown in FIG. 6. Also, since the linear velocity is slow in the inner circumference of the semiconductor wafer 104, the frequency components of the scatter reflection light 102 from the foreign matter on the surface of the semiconductor wafer 104 are concentrated on the low-frequency range as shown in FIG. 6. In other words, the frequency components of the detection signal are changed in accordance with the radius position of the semiconductor wafer 104 which is an object to be inspected.

Therefore, in the present embodiment, the response characteristics of the amplifier 301 are controlled in accordance with the radius position of the semiconductor wafer 104 as shown in FIG. 2 via the control circuit 303 and the control signal 304 based on the radius information 106 of the semiconductor wafer 104.

More specifically, with regard to the conventional detection circuit having the response characteristics unrelated to the signal components, the response characteristics of the detection circuit 300 are variably controlled in accordance with the change in the signal components based on the information having a correlation with the signal components in the present embodiment. By this means, the noise components other than the signal components which are the objects to be detected are restrained, and the highly accurate signal detection can be achieved.

Note that, although the operation principle has been simplified in the description of the foreign matter inspection apparatus for a semiconductor wafer according to the present embodiment as shown in FIG. 1 and FIG. 2, it is also possible to employ the configuration in which the response characteristics of the entire detection circuit are controlled by controlling the resistor 201 in the I-V conversion circuit 200 by use of a variable resistor and a variable capacitor.

Further, although the frequency band and the gain of the detection circuit 300 are simultaneously changed in accordance with the radius position of the semiconductor wafer in FIG. 2, since it is important to put the response characteristics of the detection circuit 300 into an optimum state including the correction of the detection signal or the detection circuit characteristics in addition to the control by detecting the speed of the object to be inspected having a correlation with the detection signal, it is needless to say that only the frequency band or only the gain can be variably controlled in accordance with the object to be detected.

Second Embodiment

Figure 3:
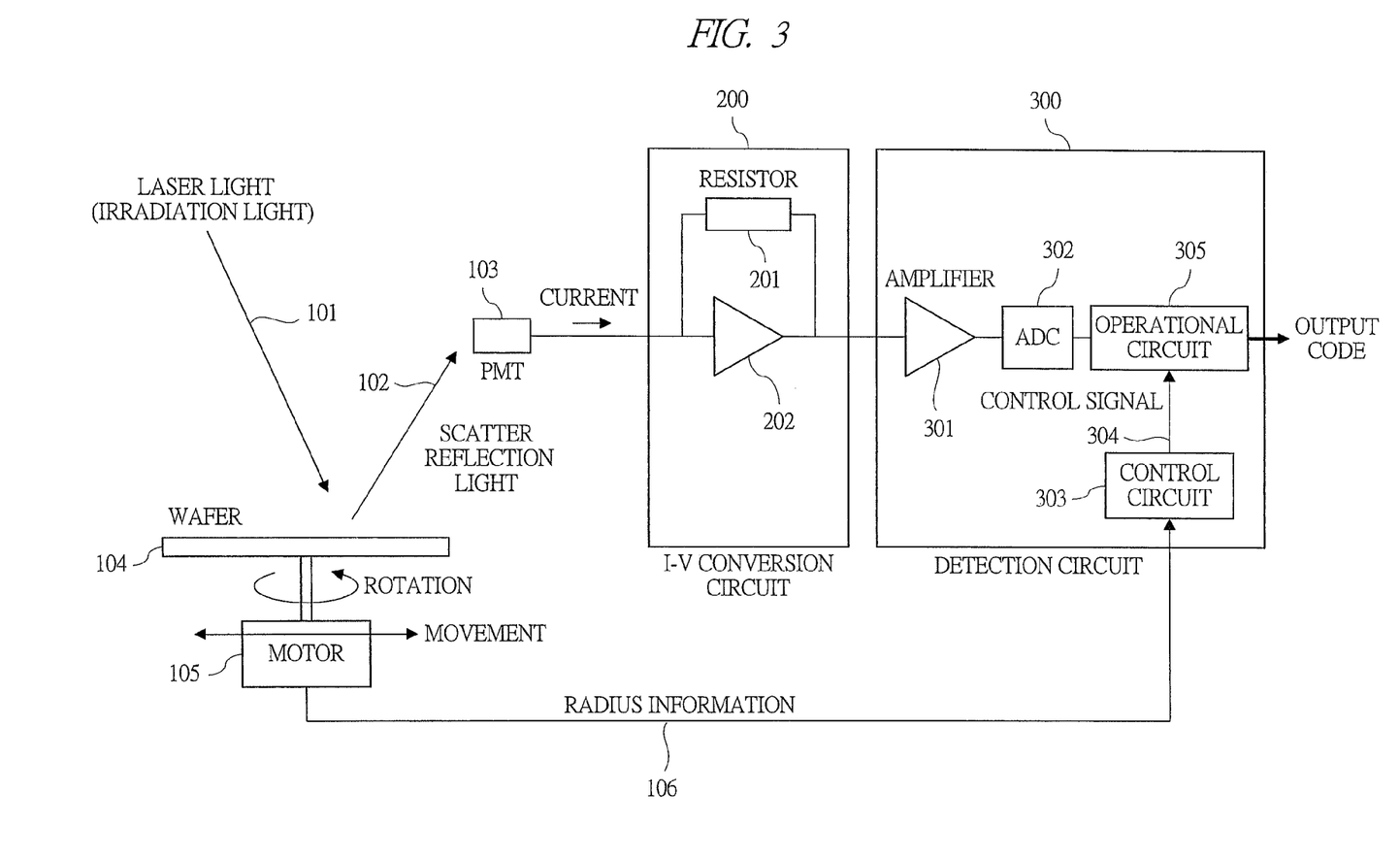
FIG. 3 is a configuration diagram showing the configuration of a foreign matter inspection apparatus for a semiconductor wafer according to the second embodiment of the present invention.
Figure 4:
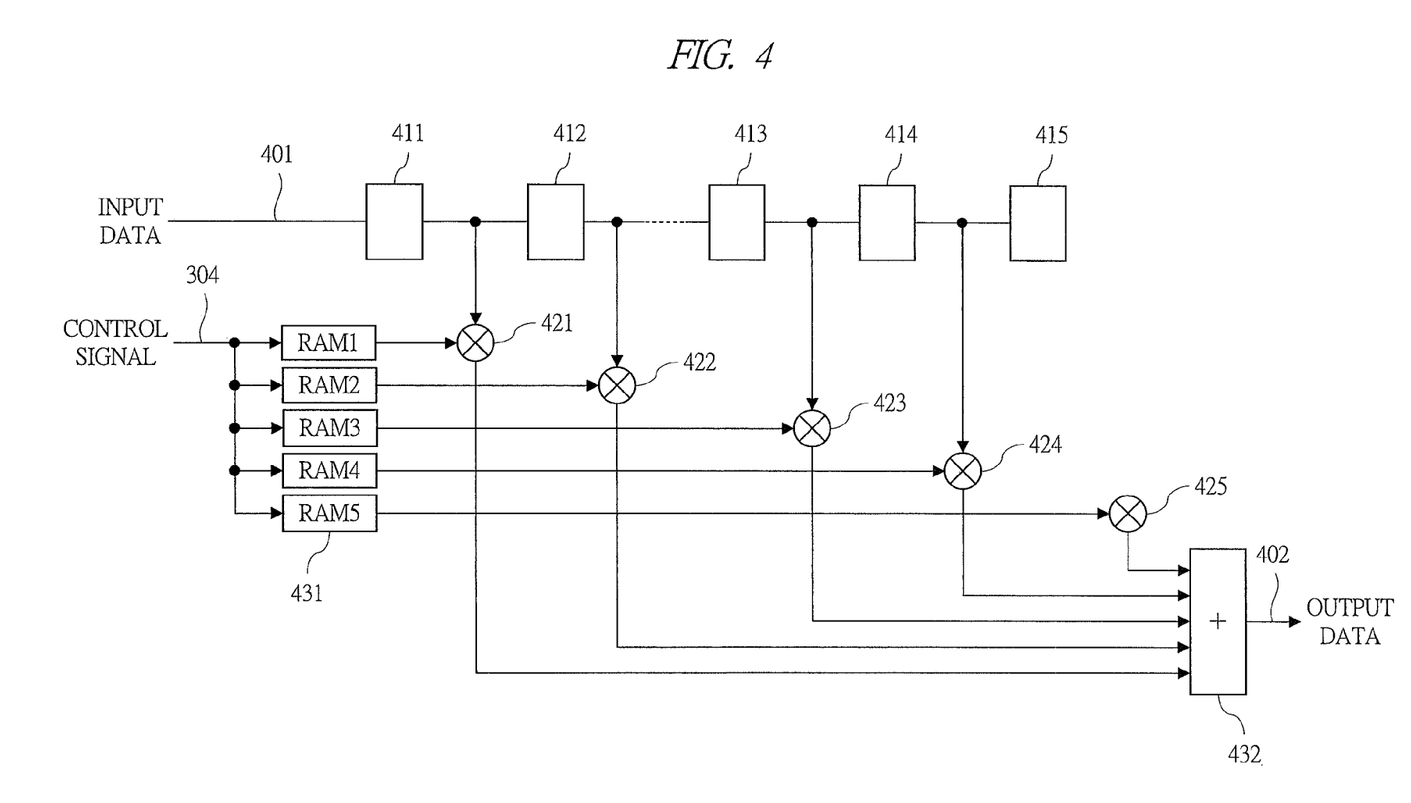
FIG. 4 is a configuration diagram showing the configuration of an operational circuit of the foreign matter inspection apparatus for a semiconductor wafer according to the second embodiment of the present invention.

The configuration and operation of the foreign matter inspection apparatus for a semiconductor wafer according to the second embodiment of the present invention will be described with reference to FIG. 3. FIG. 3 is a configuration diagram showing the configuration of the foreign matter inspection apparatus for a semiconductor wafer according to the second embodiment of the present invention, and FIG. 4 is a configuration diagram showing the configuration of an operational circuit in the foreign matter inspection apparatus for a semiconductor wafer according to the second embodiment of the present invention.

The second embodiment is characterized by comprising an operational circuit 305 in the detection circuit 300, and is the same as the first embodiment other than the operational circuit 305.

In FIG. 3, in the detection circuit 300, the output voltage of the amplifier 301 having fixed response characteristics is converted into a predetermined code by the A/D converter 302, the code output from the A/D converter 302 is subjected to an arithmetic operation by the operational circuit 305 in accordance with the control signal 304 from the control circuit 303, and then the code is output.

As the arithmetic operation in the operational circuit 305, the arithmetic operation for variably controlling the response characteristics in accordance with the control signal 304 is performed between the output code of the A/D converter 302 and the output code of the operational circuit 305 so as to have the response characteristics shown in FIG. 2.

FIG. 4 shows a configuration example of the operational circuit 305. In the operational circuit 305, the input data 401 is sequentially delayed by delay circuits 411 to 415 in accordance with an operation clock (not shown), the output data of the delay circuits 411 to 415 and the output data of the RAM 413 are multiplied by each of the multiplication circuits 421 to 425, and the output data of the multiplication circuits 421 to 425 are added up by an adder circuit 432, thereby obtaining the output data 402.

The configuration in FIG. 4 is generally known as finite impulse response (FIR) filter configuration, and response characteristics such as frequency characteristics of a circuit are changed in accordance with a coefficient to the multiplication circuit. Therefore, by inputting the control signal 304 to the address input of the RAM 431 disposed in the operational circuit 305 to change the output data of the RAM 431 in accordance with the control signal 304, the response characteristics shown in FIG. 2 can be achieved in the operational circuit 305.

Note that the arithmetic operation in the operational circuit 305 can be performed in, for example, a data processing circuit (not shown) that inputs the output code from the detection circuit 300 and determines the foreign matter or the like. In this case, by inputting the control signal 304 from the control circuit 303 to the data processing circuit, the determination of the foreign matter or the like in consideration of the response characteristics shown in FIG. 2 can be performed by the control signal 304 in the processing in the data processing circuit.

In the foregoing, the invention made by the inventors of the present invention has been concretely described based on the embodiments. However, it is needless to say that the present invention is not limited to the foregoing embodiments and various modifications and alterations can be made within the scope of the present invention.

According to the present invention, the highly accurate signal detection can be achieved and the use thereof is not limited to the foreign matter inspection apparatus directed to a semiconductor wafer as an object to be inspected, and the present invention can be applied to various detection circuits which detect a response signal from an object to be inspected.

The effects obtained by typical aspects disclosed in the present invention will be briefly described below.

That is, as the effects obtained by the typical aspects of the present invention, in a detection circuit of a foreign matter inspection apparatus for a semiconductor wafer, the signal detection can be performed with the optimum response characteristics in accordance with the condition of the detection signal based on the position information of the foreign matter, and the highly accurate foreign matter detection can be achieved.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A foreign matter inspection apparatus for a semiconductor wafer comprising:
a reflection light detector which irradiates a semiconductor wafer, which is an object to be inspected, with irradiation light and detects reflection light from the semiconductor wafer;
an amplifier which amplifies a signal based on the reflection light detected by the reflection light detector and in which response characteristics of amplification are controlled by using a control signal including radius information of the semiconductor wafer having a correlation with the reflection light and a relation between a detection circuit gain and a frequency determined in accordance with a radius position of the semiconductor wafer;
an A/D converter which converts the signal amplified by the amplifier into a predetermined code and outputs the code;
a control circuit which generates the control signal based on information of the semiconductor wafer having a correlation with the reflection light; and
a data processing circuit which detects a foreign matter on the semiconductor wafer based on the code output from the A/D converter.

2. The foreign matter inspection apparatus for semiconductor wafer according to claim 1, wherein the amplifier controls the response characteristics of the amplification by using the control signal and the relation between the detection circuit gain and the frequency in which the frequency and the detection circuit gain are decreased when being closer to an inner circumference of the semiconductor wafer and the frequency and the detection circuit gain are increased when being closer to an outer circumference.

3. A foreign matter inspection apparatus for a semiconductor wafer comprising:
- a reflection light detector which irradiates a semiconductor wafer, which is an object to be inspected, with irradiation light and detects reflection light from the semiconductor wafer;
- an amplifier which amplifies a signal detected by the reflection light detector;
- an A/D converter which converts the signal amplified by the amplifier into a predetermined code and outputs the code;
- an operational circuit which variably controls the code output from the A/D converter by using a control signal having a correlation with the reflection light and a relation between a detection circuit gain and a frequency determined in accordance with a radius position of the semiconductor wafer;
- a control circuit which generates the control signal based on information of the semiconductor wafer having a correlation with the reflection light; and
- a data processing circuit which detects a foreign matter on the semiconductor wafer based on the code which has been subjected to the arithmetic operation in the operational circuit.

4. The foreign matter inspection apparatus for a semiconductor wafer according to claim 3, wherein the operational circuit variably controls the code by using the control signal and the relation between the detection circuit gain and the frequency in which the frequency and the detection circuit gain are decreased when being closer to an inner circumference of the semiconductor wafer and the frequency and the detection circuit gain are increased when being closer to an outer circumference.

5. A foreign matter inspection apparatus for a semiconductor wafer comprising:
- a reflection light detector which irradiates a semiconductor wafer, which is an object to be inspected, with irradiation light and detects reflection light from the semiconductor wafer;
- an amplifier which amplifies a signal detected by the reflection light detector;
- an A/D converter which converts the signal amplified by the amplifier into a predetermined code and outputs the code;
- a control circuit which generates a control signal including radius information of the semiconductor wafer having a correlation with the reflection light; and
- a data processing circuit which detects a foreign matter of the semiconductor wafer based on the code output from the A/D converter and the control signal and a relation between a detection circuit gain and a frequency determined in accordance with a radius position of the semiconductor wafer.

6. The foreign matter inspection apparatus for a semiconductor wafer according to claim 5, wherein the data processing circuit detects the foreign matter of the semiconductor wafer by using the code, the control signal in which the frequency and the detection circuit gain are decreased when being closer to an inner circumference of the semiconductor wafer and the frequency and the detection circuit gain are increased when being closer to an outer circumference, and the relation between the detection circuit gain and the frequency determined in accordance with the radius position of the semiconductor wafer.

\* \* \* \* \*